United States Patent [19]
Nakamoto

[11] Patent Number: 5,653,453
[45] Date of Patent: Aug. 5, 1997

[54] COLLET CHUCK

[75] Inventor: Takayuki Nakamoto, Tokyo, Japan

[73] Assignee: Iwata Denko Co., Ltd., Tokyo, Japan

[21] Appl. No.: 582,925

[22] Filed: Jan. 4, 1996

[30] Foreign Application Priority Data

Sep. 28, 1995 [JP] Japan .................. 7-193318

[51] Int. Cl.$^6$ .................................................. B23B 31/20
[52] U.S. Cl. ................ 279/50; 279/46.3; 279/137; 433/129
[58] Field of Search ............. 279/46.3, 50, 137; 433/127, 129

[56] References Cited

U.S. PATENT DOCUMENTS 5,074,789  12/1991  Shibata ........................ 433/129

FOREIGN PATENT DOCUMENTS 751613  7/1956  United Kingdom ............ 279/46.3

Primary Examiner—Steven C. Bishop
Attorney, Agent, or Firm—Watson Cole Stevens Davis, P.L.L.C.

[57] ABSTRACT

An object of the present invention is to provide a collet chuck in which a chuck section of a collet is so formed as to provide a greater chucking force when the collet chuck is turned. To accomplish this object, a collet chuck is provided in which a collet mounted on the axis of rotation of a rotating element which rotates in one direction, and having a chuck section which is guided for closing by a guide section of a retainer which is interposed between the rotating element and the collet and moves on the axis of rotation, is adapted to hold a member to be chucked by inserting into an insertion hole of the collet, and the chuck section of the collet is formed in a spiral configuration having a plurality of slits cut from one end of the retainer side and in the opposite direction of rotation along the direction of the axis of rotation.

4 Claims, 5 Drawing Sheets

COLLET CHUCK

BACKGROUND OF THE INVENTION

The present invention relates to a collet chuck in use in dental and crafts handpieces and various types of machine tools.

In a conventional collet chuck a chuck section is formed by providing a slit section along the axial direction of a collet in a rotating element. The collet chuck is of such a mechanism that a force for chucking a member to be chucked is obtained only by centripetally moving the chuck section that has been guided to the taper surface section of the rotating element.

In the case the collet chuck is a dental handpiece for example, mounting and removal of an odontotherapeutic tool as a member to be chucked can readily performed and at the same time a chucking force corresponding to a high-speed revolution is obtainable.

It is an object of the present invention to provide a collet chuck wherein the chuck section itself in the collet has been so structured as to further provide an increased chucking force during rotation.

SUMMARY OF THE INVENTION

To accomplish the above-described object, the collet chuck in which a collet mounted on the axis of rotation of a rotating element that rotates in one direction and having a chuck section which is guided for closing by a guide section of a retainer interposed between the rotating element and the collet and moving on the axis of rotation is designed to chuck a member to be chucked by inserting into, and out of, an insertion hole of the collet; the chuck section of the collet being formed in a spiral configuration having a plurality of slit sections cut from the rear end of the retainer side and in the opposite direction of rotation along the direction of the axis of rotation. The collet chuck has the following advantage.

The spiral chuck section is closed by the retainer to hold a member to be chucked; when turned together with the rotating element, the chuck further grips the member to be chucked inserted in the insertion hole as if wrapping around the surface of the member to be chucked, thus chucking the member to be chucked with a greater chucking force.

Tool fastening and releasing operations of the spiral chuck section can readily be performed simply by pushing and releasing the retainer.

Also in the present invention the collet is of such a structure that the forward end of the insertion hole on the inlet side is fixedly connected to the rotating element side, so that the collect will rotate as one unit with the rotating element. The present invention therefore has the following advantage.

The collet rotating as one unit with the rotary body can reliably turn the member to be chucked in a chucked state.

In the present invention the collet is so designed as to be movable on the axis of rotation of the rotating element, and a second chuck section having a plurality of slits cut from the forward end of the insertion hole on the inlet side along the axis of rotation is formed in the forward end of the insertion hole and guided towards closing the chuck by the guide section in the rotating element with the closing operation of the spiral chuck section.

The present invention therefore has the following advantage.

The member to be chucked is double-chucked on the innermost side of the insertion hole by the spiral chuck section and further on the inlet side of the insertion hole by the second chuck section.

According to the present invention, the spiral chuck section is provided with an annular groove which is formed in the surface of the insertion hole adjacent to the innermost end side of the slit section. The present invention, therefore, has the following advantage.

The chuck section can easily move from the groove section when centripetally moving, thus smoothly gripping the member to be chucked with the chuck.

The helix angle in the direction of axis of rotation and number of slits of the spiral chuck section in the present invention are set with the chucking force and productivity taken into account. As a structure for guiding the spiral chuck section towards opening and closing, a guiding section of the retainer and a guided section in the chuck section are both formed tapered, or one tapered and the other convexly curved. Similarly, the guiding section of the rotating element and the guided section of the second chuck section are both formed tapered, or one tapered and the other convexly curved.

The foregoing and still further objects and advantages of the present invention will become apparent from a study of the following specification, taken in connection with the accompanying drawings.

DETAILED DESCRIPTION OF THE PREFERRED EMBODIMENT

Figure 3:
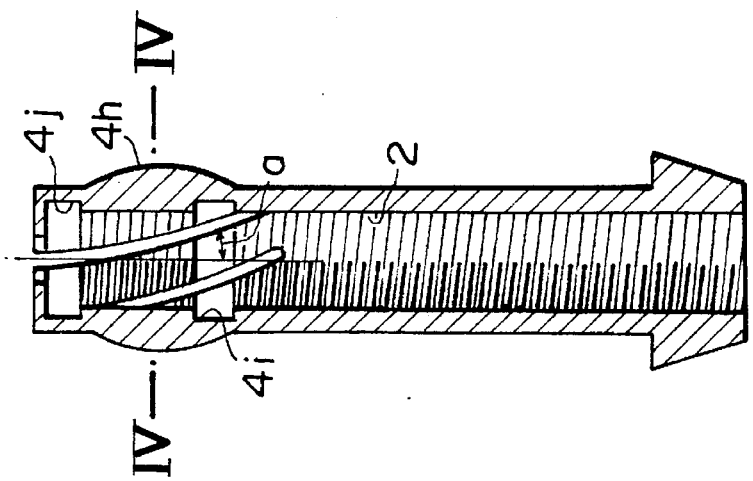
FIG. 3 is an enlarged longitudinal sectional view of the same.
Figure 2:
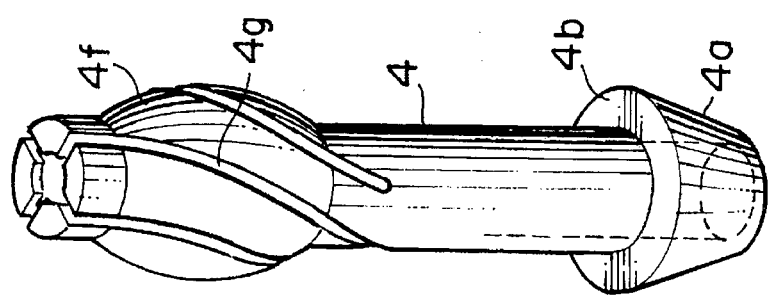
FIG. 2 is an enlarged perspective view of a collet.

FIGS. 1 to 4 show one embodiment of a collet chuck of the present invention used in a dental handpiece, wherein reference numeral 1 denotes a collet chuck; 2, a rotary body; 3, a retainer; and 4, a collet.

The rotary body 2 which is of a tube type has the retainer 3 in the upper part of the tube and the collet inside of the retainer 3, which are arranged coaxially. In the opening section 2a at the upper edge of the rotary body 2 a snap ring 5 is mounted to hold the retainer from slipping out of the opening section 2a. The guide hole section 2b at the lower end of the rotary body 2 is formed in a shape of inverted truncated cone, for guiding the forward end section 4a of the inverted truncated cone of the collet 4 by the guide hole section 2b, thereby improving the accuracy of the shaft center.

The retainer 3 is vertically movably mounted on the upper side in the rotary body 2. At the top end of a head section 3a protruding out of the opening section 2a, a projecting engaging section 3b is formed; and on the inner peripheral surface of the lower tube section 3c is formed a tapered surface section 3d having a form of an inverted truncated cone. This retainer 3 is pressed upwards by means of a coil spring 6 disposed between the lower end of the tube section 3c and the upper jaw section 4b of the forward end section 4a in the collet 4, so that the retainer 3 will be movable from the lower position to the upper position through the middle position.

The collet 4 is a cylindrical part; the insertion hole 4c is formed concentrical with the axis of rotation. In the surface of this insertion hole 4c is provided a thread section 4d in the same direction as the direction of rotation of the collet 4 (a right-hand thread on the drawing). Furthermore, the jaw section 4b is projectively formed on the upper side of the forward end section 4a of the lower end of the body 1; and in the innermost end of the insertion hole 4c at the upper end of the collet 4 is projectively formed a stopper 4e against which an odontotherapeutic tool 40 inserted in the insertion hole hits.

In the upper half section of the collet 4 is formed a spiral chuck section 4f formed spiral and having a plurality of slits 4g of spiral form cut from the upper end in an opposite direction of rotation of the rotary body 2 along the axis of rotation. The slit section has a helix angle a of about 30 degrees.

The chuck section 4f is provided with a guided section 4h formed convexly curved on the outer surface, and is radially slidable for reciprocation with an elastic recovery power.

In the insertion hole 4c an annular check groove section 4i is formed near the innermost end side of the slit section 4g in the hole surface in the position of the chuck section 4f, and also an annular escape groove 4j is formed in the hole surface section adjacent to the stopper 4e.

Furthermore, the guided section 4h of the collet 4 and the tapered surface section 3d of the retainer 3 are coated with a coating layer of low friction coefficient, for example TiCN, thereby ensuring smooth sliding.

The collet 4, with its inverted truncated conical forward end section 4a fixedly bonded to the guide hole section 2b of the rotary body 2, rotates as one unit with the rotary body 2. The guided section 4h in the chuck section 4f held in contact with the tapered surface section 3d of the retainer 3, is designed to slide inwards through the tapered surface section 3d with the vertical movement of the retainer, to thereby enable gripping the odontotherapeutic tool 40 and also reciprocating outwards with the elastic recovery force to release the tool from the chucked condition.

That is, with the retainer 3 moved downwards against the force of the spring 6, the collet chuck is capable of elastically moving and elastically recovering to the following three positions: a full-open position in which the odontotherapeutic tool 40 to be inserted into the insertion hole 4c can be released; a half-open position in which the spiral chuck section 4f pressed against the retainer 3 which is moved upwards with the force of the spring 6 can properly chuck the odontotherapeutic tool 40, and during rotation the chuck section 4f winds around the shank of the odontotherapeutic tool 40 to increase the chucking force for gripping the tool; and a closed position in which as the chuck section 4f is excessively pressed against the retainer 3 which moves upwards by the force of the spring 6, the odontotherapeutic tool 40 can not be chucked because of insufficient insertion.

FIGS. 5 to 9 show another embodiment of the collet chuck of the present invention used in a dental handpiece as an example. Its constitution is basically the same as that described above; therefore common members of the constitution will not be described.

The collet 4 of the collet chuck 1 is movable on the axis of rotation in the rotary body 2; at the forward end section 4a on the inlet side of the insertion hole 4c there is formed a second shuck section 4k having a plurality of slits 4m cut from the forward end along the axis of rotation and furthermore a truncated cone-shaped guided section 4n is formed on the outer periphery of the forward end section 4a.

The second chuck section 4k is of such a design that, with the upward movement of the collet 4, the guided section 4n is guided by the truncated cone-shaped guide section 2c of the rotary body 2, sliding inwards to grip the odontotherapeutic tool 40 and reciprocating outwards with the elastic recovery force to release the odontotherapeutic tool 40 from the chucked condition.

That is, when the collet 4 is pulled upward to the retainer 3 which moves upwards with the force of the spring 6, with the odontotherapeutic tool 40 properly chucked in the spiral chuck section 4f, the second chuck section 4k is guided by the guide section 2c towards closing, thus chucking the lower part of the shank of the odontotherapeutic tool 40 at the inlet side of the insertion hole 4c together with chucking the upper part of the shank of the odontotherapeutic tool 4 on the innermost side of the insertion hole 4c by the spiral shuck section 4f. That is, the tool 40 can be double-chucked at two places, upper and lower.

In the recess section 4p provided on the upper side of the guided section 4n of the collet 4, a ball 7 on the rotary body 2 side is fitted by the force of the spring 8, so that the collet 4 will rotate as one unit as the rotary body 2 through the medium of the ball 7.

The spring 6 is disposed between the stepped receiving section 2r of the rotary body 2 and the lower end of the tube section 3c of the retainer 3, to push the retainer 3 upwards with the spring force.

Figure 1:
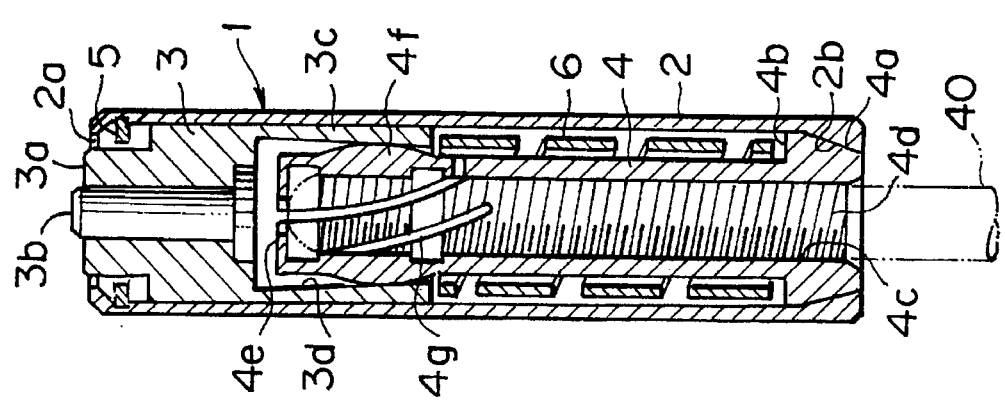
FIG. 1 is a longitudinal sectional view showing one embodiment of a collet chuck of the present invention used in a dental handpiece.
Figure 6:
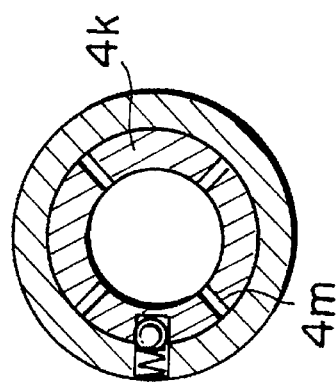
FIG. 6 is an enlarged cross sectional view taken along line (6)—(6) of FIG. 5.
Figure 10:
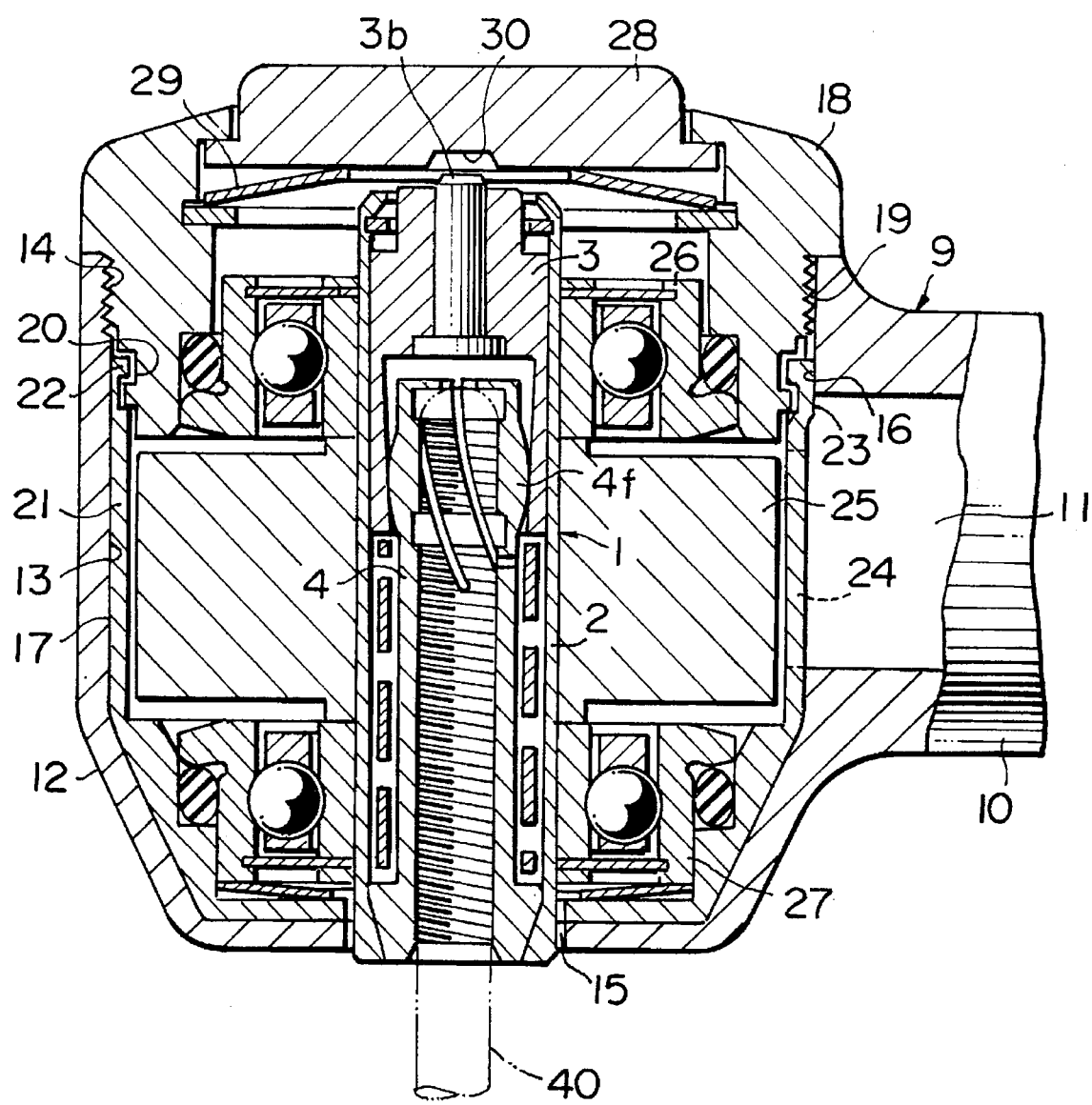
FIG. 10 is a longitudinal sectional view of the collet of FIG. 1 assembled to the dental handpiece, wherein the odontotherapeutic tool is properly chucked in a rotatable condition.
Figure 11:
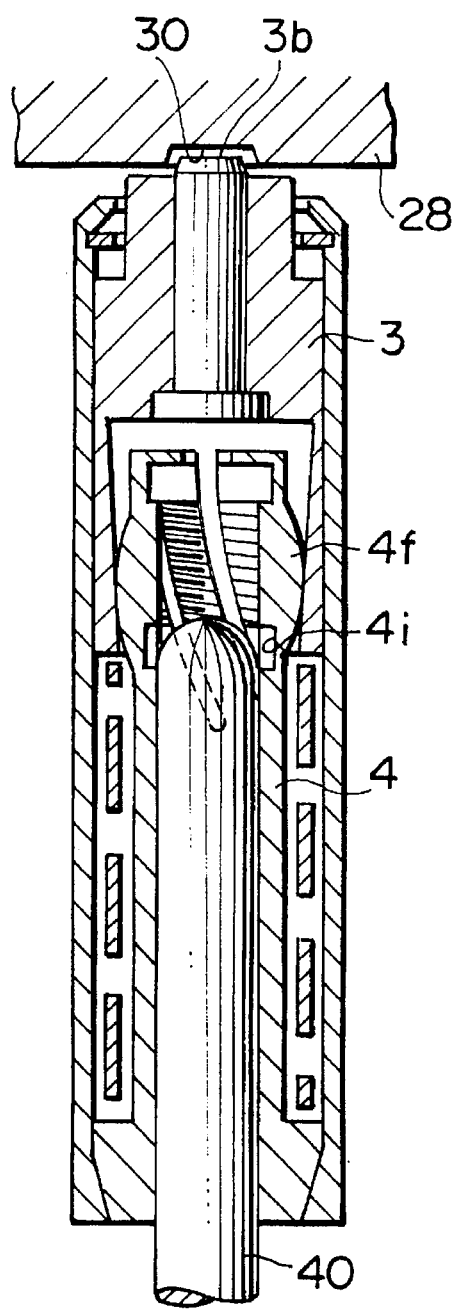
FIG. 11 is a partly enlarged longitudinal sectional view of a safety stop mechanism in operation.
Figure 12:
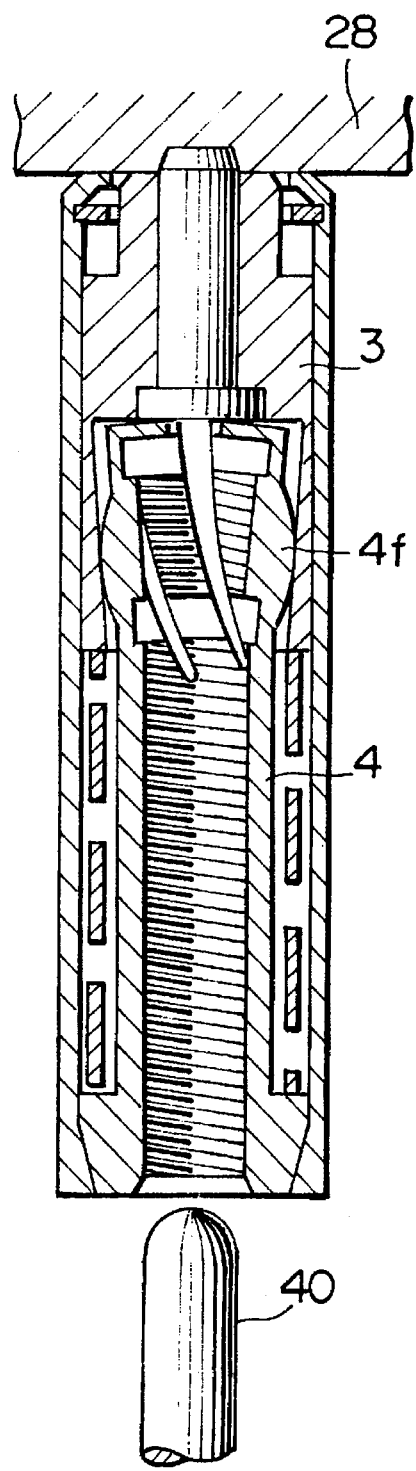
FIG. 12 is a partly enlarged longitudinal sectional view showing the condition in which the odontotherapeutic tool can be inserted in and pulled out.

FIGS. 10 to 12 show a dental handpiece 9 assembled with the collet chuck 1 of the mode shown in FIG. 1.

The handpiece body 10 has a mounting section 13 inside of a head section 12; an internal thread section 14 is formed in the opening edge of this mounting section 13; and a mouth section 15 is formed at the center of the bottom section. Inside the mounting section 13 a driving unit 17 is removably mounted by mounting an external thread section 19 of a head cap 18 in the same unit to the internal thread section 14.

The driving unit 17 is of such a construction that an annular engaging section 22 at the upper edge of a plastics case 21 is engaged with an annular engaged groove section 20 of the plastics head cap 18 in the lower side of the external thread section 19, to thereby rotatably connect the head cap 18 in one unit with the case 21, and that when the driving unit 17 is mounted on the mounting section 13, a projecting portion 23 at the top end of the case 21 is guided to a guide groove section 16 at the opening edge of the head section 12, so that the air inlet port 24 in the side surface of the case 21 will agree in a connected manner with an air supply passage 11.

Then, the rotary body 2 in the collet chuck 1 provided with vanes 25 is rotatably supported on the upper and lower bearings 26 and 27 in the head cap 18 and the case 21.

In this head cap 18 is mounted a plastics pushbutton 28 which can be pushed downwards against the force of a disk spring 29; pushing the retainer 3 downwards by means of this pushbutton 28 allows the insertion and removal of the odontotherapeutic tool 40 in relation to the chuck section 41. Also, on the back side of the head cap 18 is formed a recess-shaped engaged section 30 in which the projecting engaging section 3b is engaged; when the retainer 3 has been moved up to the upper position, the projecting engaging section 3b engages with the recess-shaped engaged section 30. The collect 4 is checked from turning by the retainer 3, thus stopping accurately.

Next, the operation of the aforesaid dental handpiece assembled with the collet chuck 1 of the embodiment shown in FIG. 1 will be explained.

When the pushbutton 28 is depressed to move the retainer 3 down to the lower position, the chuck section 4f of the collet 4 elastically turns back to the full-open position, in which the odontotherapeutic tool 40 can be inserted into, or removed from, the chuck section 4f as shown in FIG. 12.

When the odontotherapeutic tool 40 has been inserted in the chuck section 4f and this insertion has been done properly, the chuck section 4f is pushed by the retainer 3 to elastically move towards closing to the half-open position, thereby ensuring reliable chucking of the odontotherapeutic tool 40. At the same time, the chuck section 4f is checked from further closing by the odontotherapeutic tool 40 thus chucked, and accordingly prevents the upward movement of the retainer 3, which therefore will stop in the half-open position immediately before the projecting engaging section 3b engages with the recess-shaped engaged section 30 of the pushbutton 28, thus rotating in one unit with the collet 4 securely chucking the odontotherapeutic tool 40. During this rotation the spiral chuck section 4f formed in the opposite direction of rotation works to tighten the odontotherapeutic tool 40 as if wrapping around the shank of the tool 40, thus providing a greater chucking force of the tool as shown in FIG. 10.

Should the odontotherapeutic tool 40 thus properly chucked move until the top end thereof reaches the position of the groove section 4i of the chuck, a safety stop mechanism would immediately operate. That is, the chuck section 4f is pushed to elastically move by the retainer 3 which moves upwards with a spring force, reducing its diameter to the closed position as the odontotherapeutic tool 40 serving to prevent the closing of the chuck section 4f moves out of the chuck section 4f. Then, the retainer 3 is pushed up to the upper position and the projecting engaging section 3b engages with the recess-shaped engaged section 30 of the pushbutton 28, thus stopping rotation to thereby check rotation of the collet 4 and the odontotherapeutic tool 40 through the retainer 3 as shown in FIG. 11.

Also rotation of the odontotherapeutic tool 40 will similarly checked when the tool 40 is inserted insufficiently into the chuck section 4f.

Figure 5:
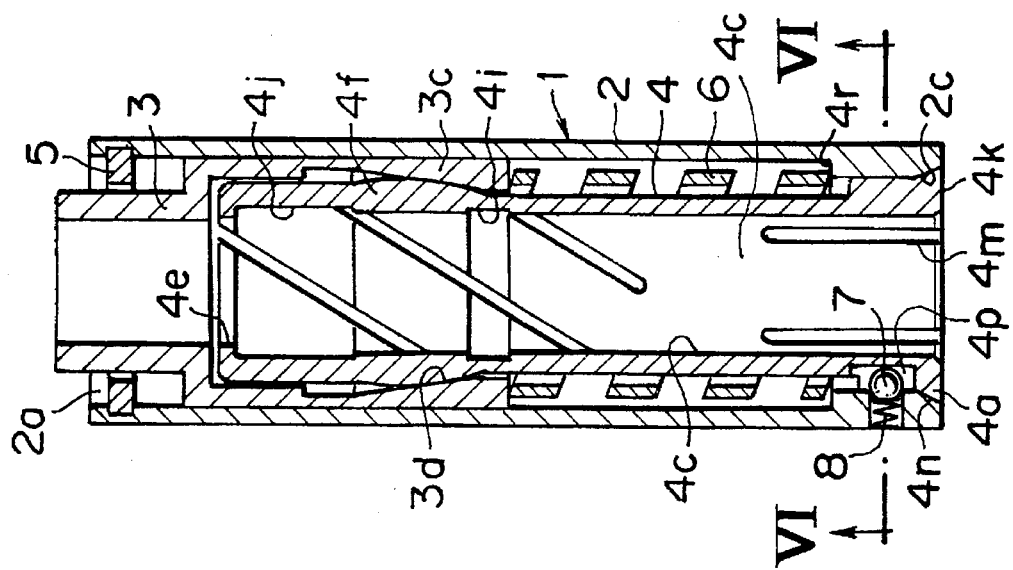
FIG. 5 is a longitudinal sectional view showing another embodiment of the collet chuck of the present invention used in the dental handpiece.
Figure 4:
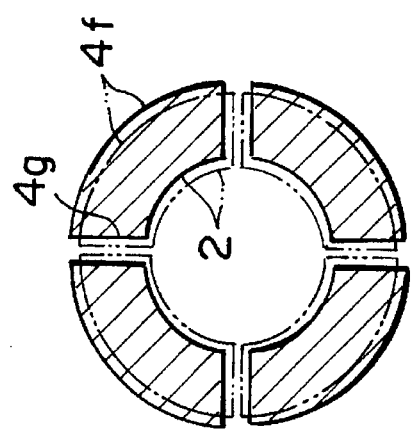
FIG. 4 is an enlarged cross sectional view taken along line (4)—(4) of FIG. 3.
Figure 9:
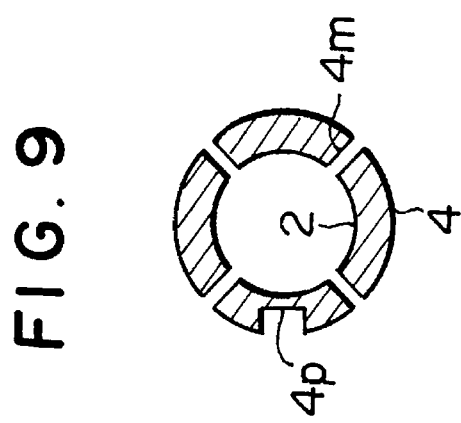
FIG. 9 is an enlarged cross sectional view taken along line (9)—(9) of FIG. 7.
Figure 8:
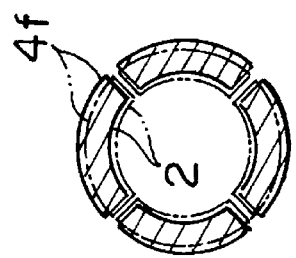
FIG. 8 is an enlarged cross sectional view taken along line (8)—(8) of FIG. 7.
Figure 7:
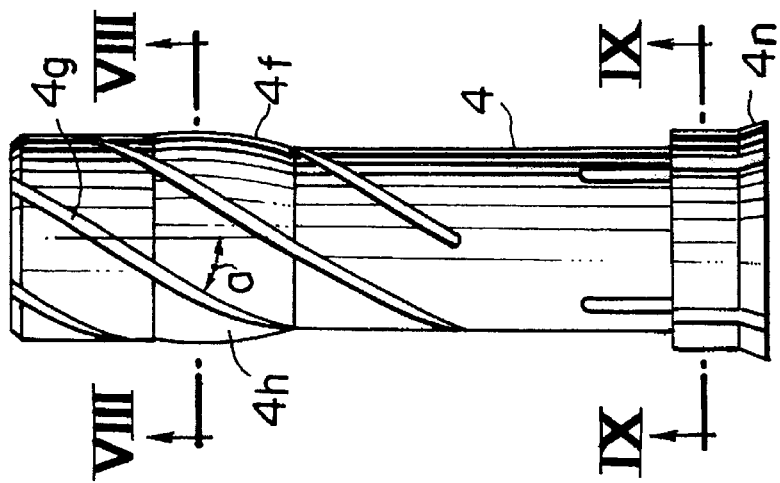
FIG. 7 is a front view of the collet.

In the dental handpiece 9 assembled with the collet chuck 1 of the embodiment shown in FIG. 5, though not illustrated, the odontotherapeutic tool 40 can be inserted into, and removed from, the spiral chuck section 4k by pushing the pushbutton 28 similarly to the handpiece assembled with the collet chuck 1 of the embodiment of FIG. 1.

The spiral chuck section 4f, at the time of chucking, securely grips the upper portion of the shank of the odontotherapeutic tool 40 and then, in a properly chucked condition, the collet 4 is pulled upwards by the force of the spring 6 through the retainer 3, guiding the second chuck section 4k towards closing by the guide section 2c, to thereby securely grip the lower portion of the shank of the odontotherapeutic tool 40. That is, the odontotherapeutic tool 40 is double-chucked firmly at upper and lower positions. Furthermore, during rotation, the spiral chuck section 4f formed in the opposite direction of rotation works to tighten the shank of the odontotherapeutic tool 40 as if wrapping around the shank surface, to provide a greater chucking force to chuck the tool.

Furthermore, since the safety stop mechanism stops rotation of the chucked tool with a frictional resistance produced when the top end of the retainer 3 pushed upwards is pressed into contact with the pushbutton 28, the collet 4 and the odontotherapeutic tool 40 are checked from turning through the retainer 3.

The rotation of the odontotherapeutic tool 40 is similarly checked if the tool 40 is inserted insufficiently into the chuck section 4f at the time of mounting of the odontotherapeutic tool 40.

Furthermore, in he collet chuck 1 of the embodiment of FIG. 1, though not illustrated, the guide hole section 2b of the rotary body 2 and the inverted truncated cone-shaped forward end 4a of the collet 4 are not fixed by bonding; in this mode the collet 4 is able to move in the direction of the axis of rotation within the rotary body 2. The collet 4, receiving the force of the coil spring 6 disposed between the bottom end of the tube section 3c of the retainer 3 and the jaw section 4b of the collet 4, is engaged, at the forward end section 4a, with the guide hole section 2b, thus rotating as one body with the rotary body 2.

Having described specific preferred embodiments of the invention with reference to the accompanying drawings, it will be appreciated that the present invention is not limited to those precise embodiments, and that various changes and modifications can be effected therein by one of ordinary skill in the art without departing from the scope and spirit of the invention as defined by the appended claims.

What is claimed is:

1. In a collet chuck in which a collet mounted on the axis of rotation of a rotating element which rotates in one direction, and having a chuck section which is guided for closing by a guide section of a retainer which is interposed between said rotating element and said collet and moves on the axis of rotation, is adapted to chuck a member to be chucked by inserting into, and out of, an insertion hole of said collet, said chuck section of said collet is formed in a spiral configuration having a plurality of slits cut from one end of said retainer side and in the opposite direction of rotation along the direction of the axis of rotation, wherein said collet is movable on the axis of rotation of said rotating element, and a second chuck section having a plurality of slit sections cut from said forward end on the inlet side of said insertion hole along the axis of rotation is formed at said forward end to close said collet chuck when guided by a guide section in said rotating element with the closing operation of said spiral chuck section.

2. A collet chuck as claimed in claim 1, wherein said collet is securely connected at the forward end on the inlet side of said insertion hole with said rotating element side and is rotatable as one body with said rotating element.

3. In a collet chuck in which a collet mounted on the axis of rotation of a rotating element which rotates in one direction, and having a chuck section which is guided for closing by a guide section of a retainer which is interposed between said rotating element and said collet and moves on the axis of rotation, is adapted to chuck a member to be chucked by inserting into, and out of, an insertion hole of said collet, said chuck section of said collet is formed in a spiral configuration having a plurality of slits cut from one end of said retainer side and in the opposite direction of rotation along the direction of the axis of rotation, wherein said spiral chuck section is provided with an annular groove section in the surface of said insertion hole near the innermost end side of said slit section.

4. A collet chuck as claimed in claim 3, wherein said collet is securely connected at the forward end on the inlet side of said insertion hole with said rotating element side and is rotatable as one body with said rotating element.

* * * * *